United States Patent [19]

Valentini

[11] Patent Number: 5,759,205
[45] Date of Patent: Jun. 2, 1998

[54] NEGATIVELY CHARGED POLYMERIC ELECTRET IMPLANT

[75] Inventor: Robert F. Valentini, Warwick, R.I.

[73] Assignee: Brown University Research Foundation, Providence, R.I.

[21] Appl. No.: 377,523

[22] Filed: Jan. 20, 1995

Related U.S. Application Data

[63] Continuation-in-part of Ser. No. 184,292, Jan. 21, 1994, abandoned.

[51] Int. Cl.$^6$ .................................................. A61F 2/28
[52] U.S. Cl. .......................... 623/16; 623/11; 623/22; 433/173; 433/201.1
[58] Field of Search ........................... 623/11, 16, 18, 623/22, 23; 433/201.1, 173

[56] References Cited

U.S. PATENT DOCUMENTS

| | | | |
|---|---|---|---|
| 3,609,768 | 10/1971 | Ayres | 3/1 |
| 3,723,754 | 3/1973 | Murayama et al. | 307/88 |
| 3,968,790 | 7/1976 | Fukada et al. | 128/82.1 |
| 3,992,725 | 11/1976 | Homsy | 3/1 |
| 4,202,055 | 5/1980 | Reiner et al. | 3/1.91 |
| 4,268,653 | 5/1981 | Uchidoi et al. | 526/255 |
| 4,668,449 | 5/1987 | Soni et al. | 264/22 |
| 4,738,740 | 4/1988 | Pinchuk et al. | 156/167 |
| 4,789,634 | 12/1988 | Müller-Lierheim et al. | 435/288 |
| 4,795,475 | 1/1989 | Walker | 623/66 |
| 4,828,563 | 5/1989 | Muller-Liekheim | 623/16 |
| 4,836,884 | 6/1989 | McAuslan | 156/629 |
| 4,919,659 | 4/1990 | Horbett et al. | 623/1 |
| 4,946,903 | 8/1990 | Gardelia, Jr. et al. | 525/326.4 |
| 4,988,358 | 1/1991 | Eppley et al. | 623/16 |
| 5,030,225 | 7/1991 | Aebischer et al. | 606/152 |
| 5,061,750 | 10/1991 | Feijan et al. | 525/54.1 |
| 5,085,632 | 2/1992 | Ikada et al. | 604/29 |
| 5,092,871 | 3/1992 | Aebischer et al. | 606/152 |
| 5,164,187 | 11/1992 | Constantz et al. | 424/423 |
| 5,266,309 | 11/1993 | Gardella, Jr. et al. | 424/78.09 |
| 5,298,602 | 3/1994 | Shikinami et al. | 528/361 |
| 5,306,311 | 4/1994 | Stone et al. | 623/18 |
| 5,311,884 | 5/1994 | Scopelianos | 128/898 |

FOREIGN PATENT DOCUMENTS

| | | |
|---|---|---|
| A-64815/86 | 11/1986 | Australia. |
| 974665 | 9/1975 | Canada. |
| 0 531 547 | 3/1993 | European Pat. Off.. |
| 0 627 227 | 12/1994 | European Pat. Off.. |

OTHER PUBLICATIONS

Aebischer, P. et al., "Piezoelectric guidance channels enhance regeneration in the mouse sciatic nerve after axotomy" *Brain Research*, vol. 436, pp. 165–168, 1987.

Bening, R.C., "Surface Modification of Poly(tetrafluoroethylene–co–hexafluoropropylene). Introduction of Alcohol Functionality" *Macromolecules*, vol. 23, pp. 2648–2655, 1990.

Davies, J.E., "The Importance and Measurement of Surface Charge Species in Cell Behaviour at the Biomaterial Interface" in *Surface Characterization of Biomaterials*, B.D. Ratner (ed.), pp. 219–234, Amsterdam: Elsevier Science Publishers B.V., 1988.

DeRossi, D.E. et al., "The Electromechanical Connection: Piezoelectric Polymers in Artificial Organs" *ASAIO* (Reprint), vol. 6, No. 1, pp. 1–11, 1983.

(List continued on next page.)

*Primary Examiner*—John G. Weiss
*Assistant Examiner*—Bruce E. Snow
*Attorney, Agent, or Firm*—Thomas J. Engellenner; Scott D. Rothenberger; Lahive & Cockfield, LLP

[57] ABSTRACT

A biocompatible implant having improved host tissue ingrowth capability and enhanced blood compatibility comprises at least one tissue-contacting surface of an electrically charged material. The electrically charged material can be further chemically modified with covalently bonded activator molecules which further promote host tissue ingrowth and adhesion to the implant and/or enhance blood compatibility.

19 Claims, 3 Drawing Sheets

OTHER PUBLICATIONS

Fukada, E., Piezoelectricity of Bone and Osteogenesis by Piezoelectric Films, in *Mechanisms of Growth Control*, R.O. Becker and C.C. Thomas (eds.), pp. 192–210, 1981.

Inoue, S. et al., "Electric Stimulation of Osteogenesis in the Rat: Amperage of Three Different Stimulation Methods" in *Electrical Properties of Bone and Cartilage*, C.T. Brighton, J. Black and S. Pollack (eds.), pp. 199–213, Grune & Stratton, 1979.

Lovinger, A.J., "Ferroelectric Polymers" *Science*, vol. 220, No. 4602, pp. 1115–1121, 1983.

Pierschbacher, M.D. and E. Ruoslahti, "Cell attachment activity of fibronectin can be duplicated by small synthetic fragments of the molecules" *Nature*, vol. 309, pp. 30–33, 1984.

Ruoslahti, E. and M.D. Perschbacher, "New Perspectives in Cell Adhesion: RGD and Integrins" *Science*, vol. 238, pp. 491–497, 1987.

Shelton, R.M. and J.E. Davies, "Osteoblast Reactions to Charged Polymers" in *The Bone–Biomaterial Interface;* J.E. Davies (ed.), pp. 181–198, Toronto: U. Toronto Press, 1991.

Shoichet, M. and T.J. McCarthy, "Surface Modification of Poly (tetrafluoroethylene–co–hexafluoropropylene) Film by Adsorption of Poly(L–lysine) from Aqeusous Solution" *Macromolecules*, vol. 24, pp. 1441–1442, 1991.

Valentini, R.F. et al., "Electrically charged polymeric substrates enhance nerve fibre outgrowth in vitro" *Biomaterials*, vol. 13, No. 1, pp. 183–190, 1992.

Valentini, R.F. et al., "Patterned neuronal attachment and outgrowth on surface modified, electrically charged fluoropolymer substrates" *J. Biomater. Sci., Polymer Edn.*, vol. 5, Nos. 1 & 2, pp. 13–36, 1993.

Valentini, R.F. et al., "Polymer electret guidance channels enhance peripheral nerve regeneration in mice" *Brain Research*, vol. 480, pp. 300–304, 1989.

5,759,205

NEGATIVELY CHARGED POLYMERIC ELECTRET IMPLANT

RELATED APPLICATIONS

This application is a continuation-in-part application of United States Ser. No. 08/184,292, filed, Jan. 21, 1994 now abandoned the contents of which are incorporated herein by reference.

BACKGROUND OF THE INVENTION

The invention relates to implantable prosthetic devices and particularly to improved materials for orthopedic and other medical implants.

Bone trauma and degenerative disease create a tremendous need for orthopedic implants which are used to replace or augment damaged tissue. Because of the stresses that many of these implants must endure, the implant materials often must be strong as well as biocompatible. A number of implant materials have been developed which meet these demands of strength and biocompatibility. The materials now used for orthopedic implants include stainless steel, titanium based alloys, and ceramics. However, these materials generally do not provide a good substrate for host tissue attachment and ingrowth. Thus, despite progress in the development of orthopedic and dental implants, the failure rate of these devices remains high because the implant materials do not promote host tissue growth, frequently resulting in loosening of the implant over time at its interface with the host tissue.

At the present time, surgeons use polymethyl methacrylate (PMMA) bone cement to fix implantable prosthetic devices to host tissue. In the short term, this cement can elicit serious side effects such as toxic or anaphylactic shock or the development of multiple blood emboli. In the long term, the cemented bone-prosthesis interface may degenerate. Such degeneration occurs as a result of host resorption of tissue near the cemented interface and the growth of a soft fibrous tissue capsule (scar tissue) around the implant. The development of this fibrous tissue capsule results in loosening of the implant within the host and eventual failure of the implant. The cement itself may also weaken and fail, resulting in loosening of the implant.

An alternative method for securing a prosthesis to host tissue involves the use of a porous coating on the implant which allows tissue growth into the interstices of the implant surface. However, this method has had variable success because the tissue grows into the pores of the coating in an unpredictable manner and does not attach to the implant itself. Without cell adherence to the implant material, the specter of implant weakening and failure remains. Moreover, the slow rate of tissue ingrowth into the implant necessitates longer periods of patient immobility, with attendant complications.

Recent work has focused on the development of surfaces for orthopedic implants which promote the attachment of bone cells to the implant. Emphasis has been on the addition of sub-surface charges and surface modification of the bone-contacting surface of the implants.

For example, in an article by J. E. Davies, "The Importance and Measurement of Surface Charge Species in Cell Behaviour at the Biomaterial Interface," *Surface Characterization of Biomaterials*, B. D. Ratner, ed., pp. 219–234 (1988), Davies found that a charged substrate can influence bone cell growth in vitro. U.S. Pat. No. 4,795,475 to Walker discloses the use of biocompatible organic polymers substituted with carbon, sulfur or phosphorous oxyacid groups which can promote osteogenesis at the host-implant interface. U.S. Pat. No. 4,828,563 to Muller-Lierheim discloses the covalent bonding of growth factors or antibodies to the implant surface. U.S. Pat. No. 4,202,055 to Reiner et al. discloses In anchorage for an orthopedic prosthesis which creates calcium phosphate coated pores in a polymer, and Australian Patent Application AU-A-64,815/86 by Kelly and Howlett discloses the modification of the surface chemistry of a prosthetic device by implanting particular ion species onto its surface either to encourage or discourage tissue ingrowth.

Several techniques for modifying the surface of fluoropolymers have been described. For example, Shoicet and McCarthy in *Macromolecules* 24:1441–1442 (1991) disciose the simple adsorption of proteins or other biological material to fluoropolymers, including fluorinated ethylene propylene copolymer (FEP). Bening and McCarthy in *Macromolecules* 23:2468 (1990) disclose the use of reducing agents to introduce hydroxyl and carboxylic acid groups to the surfaces of polyvinylidene fluoride (PVDF) and FEP. Also, U.S. Pat. No. 4,946,903 to Gardella, Jr. et al. discloses the use of glow discharge techniques to modify wettability and surface tension of fluoropolymers.

These advances have not solved the problem of creating a durable host-implant bond. Moreover, charged coatings that promote long-term attachment of tissue to the implant and minimize non-specific attachment of other types of cells and biological material have not been described. Further, none of the above-mentioned techniques addresses the need for cell-specific modification of fluoropolymer coatings. Also, with respect to vascular implants, endothelialization of vascular implant walls, crucial to the prevention of blood clot formation, does not take place on the surface of materials currently available. The absence of endothelial cells on vascular prostheses limits the use of such implants in smaller diameter (less than 4–6 mm) applications. Thus, electret materials which encourage endothelial cell growth on the surface of the prosthesis would improve currently available vascular implants and allow the use of smaller diameter synthetic vessels. Thus, the need exists for an implantable prosthetic device having a biocompatible surface which promotes tissue ingrowth at the host-implant interface.

It is therefore an object of this invention to provide a surface coating for implantable prosthetic devices which will promote a superior host-implant bond, thus improving the durability and lifetime of the prosthesis and enhancing patient mobility and comfort.

SUMMARY OF THE INVENTION

The invention provides a biocompatible implant having an electrically charged tissue-contacting surface which encourages host tissue ingrowth and adherence to the implant and which promotes host tissue regeneration. The electrically charged implant surface promotes a more secure attachment of the host tissue to the implant than that which is provided by currently available materials. In one embodiment, electrically charged fluoropolymers with surface-coupled attachment factors are disclosed for implant materials.

In accordance with one aspect of the invention, there is provided a biocompatible implant having improved host tissue compatibility and ingrowth capability. The implant comprises at least one tissue-contacting surface of an electrically charged material.

In accordance with another aspect of the invention, there is provided a biocompatible implant having improved host tissue compatibility and ingrowth capability as described above, wherein the tissue-contacting surfaces of the implant consist essentially of an electrically charged material which has been chemically modified with covalently bonded activator molecules which further promote host tissue ingrowth and adhesion to the implant.

In accordance with still another aspect of the invention, there is provided a method of making a biocompatible implant having improved host tissue compatibility and ingrowth capability. The method comprises the steps of: providing an implant having at least one tissue-contacting surface comprising a fluoropolymer, and providing an electrical charge to the fluoropolymer.

In accordance with still another aspect of the invention, there is provided a method of making a biocompatible implant having improved host tissue compatibility and ingrowth capability as described above, wherein activator molecules which further promote host tissue ingrowth and adhesion to the implant are covalently bonded to the electrically charged fluoropolymer.

In yet another aspect of the invention, the biocompatible implants of the present invention can be used for various other purposes for which it is desirable to promote tissue growth and implant incorporation into a patient's body. For example, in addition to orthopedic applications, including hip, knee, shoulder and elbow replacements, the materials of the present invention can be used for soft tissue implants, such as breast prostheses, percutaneous implants and vascular implants, including vascular grafts and vascular stents. The materials of the present invention can also be used for mandibular ridge reconstruction, dental implants, such as posts and rakes for artificial teeth, as membranes for use in guided tissue regeneration, as coatings for posts and rakes for artificial teeth. In addition, the materials of the invention can be used for tendon and ligament prostheses, digit (e.g., finger or toe) prostheses, permanent structural prostheses, such as spinal fusion implants, sutures for tissue apposition, and dressing materials for skin wounds including ulcers and burns, and the like. Alternatively, the materials of the invention can be used in cosmetic or reconstructive surgery to promote tissue growth and regeneration.

The invention will next be described in connection with certain illustrated embodiments. However, it should be clear that various modifications, additions and subtractions may be made without departing from the spirit or scope of the invention.

BRIEF DESCRIPTION OF THE DRAWINGS

The invention is more fully understood from the following description when read together with the accompanying drawings in which.

DETAILED DESCRIPTION OF THE INVENTION

Figure 1:
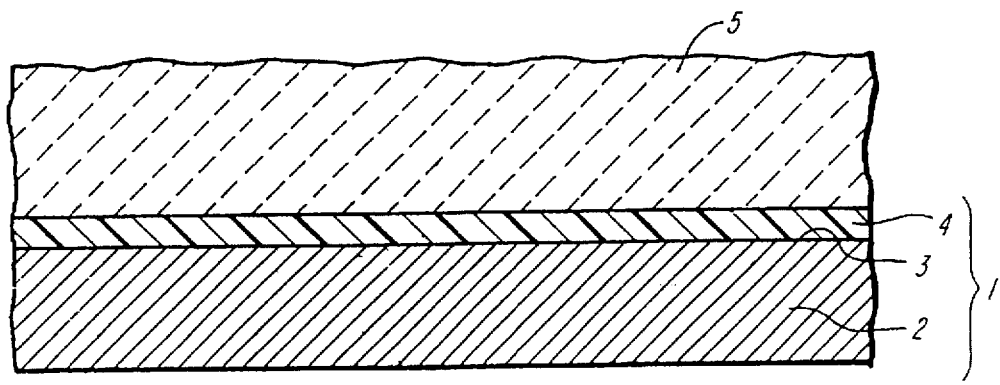
FIG. 1 is a generalized cross-section of an interface between a prosthetic implant and its host environment according to the invention.

The electrically charged materials used in the invention can be electrets or other materials which have the capacity to store electrical charge. The term "electret", as used herein, refers to a nonpolar dielectric material which is characterized by a permanent or quasi-permanent bulk monopolar charge which produces an external electrostatic field. The term "electret" is intended to broadly encompass both natural and synthetic materials displaying surface electrical charge storage capacities.

Electrets can be classified into two broad categories of materials which are distinguishable by their charge storage mechanisms. A "permanent" electret is a nonpolar dielectric material which produces an external electrostatic field as a result of trapped monopolar charges within its bulk and subsurface regions. Neutralization of internal bulk charges is prevented by the inherently low internal conductance of the electret. The trapped electrical charges can be either positive or negative.

In contrast, a "piezoelectric" material is a polar dielectric electret which contains molecular dipoles. Under static conditions no external electrostatic field is exhibited by piezoelectric materials because the mobility of the dipole charges in this relatively conductive material has a neutralizing effect. However, when a piezoelectric material is mechanically deformed or strained, dipole movement within the material causes a temporary charge imbalance. This charge imbalance while the material is in dynamic strain produces transient electric charges within the material.

Prosthetic devices which are coated with these electrically charged materials promote the growth of new host tissue around the implanted device and the adherence of this new tissue to the device. Because the bulk charges of these materials can be manipulated without concomitant alteration of their surface chemistry, the surface charge can be designed to optimize host cell growth and attachment to the implant or to promote regeneration of adjacent tissues.

The term "surface", as used herein, is intended to encompass the tissue-contacting region of an implantable device which extends from the exterior surface to a depth of approximately 100 angstroms, as well as subsurface regions which extend from a depth of approximately 100 angstroms to approximately 10 micrometers. In the case of porous structures, the surface includes all open void spaces of the interior portion of the structure, as well as the exterior portion.

The term "tissue-contacting", as used herein, is intended to encompass those surfaces of a biocompatible implant, or an electrically charged coating on a biocompatible implant, which come in contact with living host tissue of any kind, including but not limited to bone, cartilage, tendons, ligaments, blood and soft tissue.

The term "host tissue", as used herein, is intended to encompass the physiological environment within a patient in which the biocompatible implants described in this invention are used, including but not limited to bone, cartilage, tendons, ligaments, blood and soft tissue.

The physical flexibility, biocompatibility and charge storage capacity of certain fluoropolymers make them especially desirable as surface coatings for orthopedic implants. Fluoropolymers are particularly useful as electret materials because they possess a. high degree of charge storage capability as well as tremendous physical strength, flexibility and biocompatibility. A preferred fluoropolymer electret material is fluorinated ethylenepropylene copolymer (FEP). FEP can store either positive or negative monopolar charges to produce an external static electric field.

Other materials capable of storing electrical charges and thus suitable for use in this invention include polytetrafluoroethylene (PTFE), and piezoelectric fluoropolymers such as polyvinylidenefluoride (PVDF) and polyvinylidenefluoride-trifluoroethylene copolymer (P(VDF-TrFE)).

The electrically charged material can be either negatively or positively charged. Osteoblasts, or bone cells, grow and adhere better to negatively charged FEP than to uncharged FEP or positively charged FEP. However, other tissue types can grow and adhere better to positively charged electret materials. For example, fibroblasts, the cells which cause growth of soft fibrous (scar) tissue at host tissue-implant interfaces, do not grow as readily on negatively-charged materials. For enhanced ingrowth of osteoblasts, the electrically charged material is preferably a negatively charged electret material, having a preferred average surface charge density on the order of approximately −1000 volts surface potential.

The invention further includes a method of making a biocompatible implant having an electrically charged surface. A biocompatible implant comprising a fluoropolymer and having at least one tissue-contacting surface is provided, and an electrical charge is imparted to the fluoropolymer. By masking the implant surface with any desired pattern, it is also possible to incorporate positively-charged, negatively-charged and even neutral, or uncharged, regions on a single coated implant.

Alternatively, a fluoropolymer coating can be deposited onto the tissue-contacting surfaces of the implant by plasma spray, plasma polymerization, or other deposition techniques. Both dense and porous coatings can be deposited. The fluoropolymer coating can then be electrically charged using corona charge injection techniques known in the art.

In another embodiment of the invention, the electrically charged fluoropolymer or fluoropolymer coating can be further modified with covalently bonded activator molecules to promote cell growth and adherence to the implant. For example, hydroxyl (OH), primary amine ($NH_2$), carboxyl (COOH) or sulthydryl (SH) groups can be covalently bonded to the fluoropolymer surface. Furthermore, the reactive OH, $NH_2$, COOH or SH surface groups can be used to couple more potent biologically active molecules to the electrically charged fluoropolymer. For example, short peptides with biological activity, such as the RGD (arginine-glycine-aspartic acid) and GRGDS (glycine-arginine-glycine-aspartic acid-serine) peptide fragments of the extracellular matrix molecule fibronectin, and the YIGSR (tyrosine-isoleucine-glycine-serine-arginine) peptide fragment of the extracellular matrix molecule laminin, can be covalently attached to the surface of an electret material to enhance tissue growth and attachment to a prosthetic implant coated with the electret material. Also, the electret material surface can be modified by the addition of biologically active molecules, such as cell attachment factors, fibroblast growth factors (FGF), platelet-derived growth factors (PDGF), transforming growth factor beta (TGF-β) and adhesion molecules, antibodies, proteins and morphogenic factors, including bone morphogenic proteins (BMP), to stimulate cell growth or differentiation.

The flexibility of the chemical and physical properties of fluoropolymers permits the optimization of polymer characteristics for a variety of biomedical uses. For example, the use of these electret materials on the bone-contacting surface of a dental prosthesis improves attachment of the implant to host tissue and increase the longevity of the implant. Also, electret materials used in tendon replacement improves the strength and durability of the bone-tendon bond.

Finally, these materials also promote better integration of other types of implants, including soft tissue implants such as breast implants, into the host. Soft tissue implants often become walled off from host tissue by a fibrous tissue capsule which leads to infection, tissue destruction and implant failure. Encouraging host cell ingrowth into the implant alleviates these problems and extends the life of the implant.

FIG. 1 shows generally a tissue-implant interface. A biocompatible implant 1 includes a structural support portion 2 having tissue-contacting surface 3 which is coated with a fluoropolymer layer 4 which can be electrically charged and chemically modified according to the present invention. Thus, the fluoropolymer coating forms an interface between the host tissue 5 and the implant 1. The fluoropolymer coating 4 on the tissue-contacting surface 3 of the implant can be either dense or porous. Porous coatings provide a three-dimensional surface structure, or scaffold, for host tissue ingrowth. The host tissue 5 can be, for example, bone, skin, vascular tissue, ligaments, tendons, or other soft tissue.

The tissue-contacting surface 3 is coated with a layer of a fluoropolymer electret material 4 which can be endowed with a transient or static electrical charge. Electret materials are attractive for in vivo applications since they can be fabricated from biocompatible polymers and can produce electrical charges without an external power source.

To generate and contain these electrical charges, the electret materials of the present invention are preferably created by charge injection using a corona-charging apparatus. The charge injection process produces either negative or positive charge accumulation in the material; however, in contrast to the radio frequency glow discharge process disclosed in U.S. Pat. No. 4,946,903 to Gardella, Jr. et al., the charge injection process does not alter the surface chemistry or surface energy of the polymer. Alternative techniques for generating and containing electrical charges are known in the art and include electron beam bombardment, irradiation, and ion beam bombardment. Where piezoelectric materials are employed, the electrical charge can be generated and trapped in the material by orienting the dipoles in the material via exposure of the material to a non-breakdown, high voltage field. The oriented dipoles generate a transient electrical charge upon mechanical deformation of the piezoelectric material.

Materials useful in the present invention include both natural and synthetic materials which are preferably biocompatible and/or biodegradable. For example, particularly useful in the present invention are polymeric materials, e.g., fluoropolymers such as fluorinated ethylenepropylene copolymer (FEP), polytetrafluoroethylene (PTFE), polyvinylidenefluoride (PVDF), and polyvinylidene-trifluoroethylene copolymer (P(VDF-TrFE), other polymers such as polyglycolic acid, polylactic acid, polyurethane, polyethylene, polysulfone, polystyrene, polyester, e.g., biodegradable polyesters, polyamides (e.g., nylon), polymethyl methacrylate, polypropylene, polyethylene terephthalate, or mixtures thereof. Synthetic polypeptides, e.g., peptides which are biological in structure but produced synthetically, e.g., polybenzyl glutamate, can also be used as materials of the present invention. Although fluoropolymers, in particular FEP, are preferred electret materials for orthopedic implant surfaces, the invention can be practiced using any electrically charged biocompatible and/or biodegradable material.

The electrically charged material can be further modified by covalently bonding chemical groups to the surface of the material. These chemical groups can include, but need not be limited to, hydroxyl (OH), primary amine ($NH_2$), carboxyl (COOH) and sulfhydryl (SH) groups. Furthermore, biologically active substances, e.g., proteins and peptides, such as growth factors, cell attachment factors, antibodies, and adhesion molecules can be coupled to these covalently bound chemical groups or directly to the surface of the material. For example, the RGD, RGDS and GRGDS peptide fragments of fibronectin, the vitronectin RGDV peptide fragment, and the laminin YIGSR peptide fragment are known to facilitate cell adhesion to polymer surfaces. Coating the surface of a prosthetic implant with these peptides can further improve host cell adhesion to the implant. Growth factors such as bone morphogenic proteins can enhance cell growth and adhesion to the electrically-charged surface. Also, antibodies can be attached to the electrically-charged surface to promote very specific attachment of certain cells to the surface. Surface modification of the materials of the present invention can also alter the biological activity of cells. For example, such surface modifications can increase or decrease the level of substances, e.g., proteins, produced and/or secreted by host tissue cells.

The invention further encompasses methods of making a biocompatible implant having improved host tissue compatibility and ingrowth capability. A biocompatible implant comprising a fluoropolymer and having at least one tissue-contacting surface is provided.

The fluoropolymer is then electrically charged. Alternatively, a biocompatible implant having a core structural portion can be coated on one or more of its tissue-contacting surfaces with a fluoropolymer material which can then be electrically charged and further modified with covalently bonded chemical groups or activator molecules.

Fluoropolymers can be stably coated onto virtually any material, including metals, other polymers, ceramics, silicon substrates and other materials, by plasma polymerization. In plasma polymerization, the monomer carbon tetrafluoride ($CF_4$) is first introduced into a glow discharge chamber which contains the implant to be coated. The plasma forms a polymeric deposit on the surfaces of the implant. The thickness of the polymeric coating can be controlled by controlling the length of time the implant is exposed to the plasma.

Generally, a thickness of from at least about 5 angstroms to at least about 10 micrometers is preferred.

Polymer coatings can alternatively be applied to the surfaces of the implant by dipping or spraying a volatile solution containing the polymer onto the surfaces of the implant using techniques known in the art. Coatings can also be applied to the surfaces of the implant through heating and shrink wrapping.

Once the fluoropolymer implant has been created, or the fluoropolymer material has been deposited onto the tissue-contacting surfaces of the implant, the fluoropolymer or fluoropolymer coating can then be loaded with either a net positive or net negative charge, or a combination of both positive and negative charges according to a desired pattern, by corona charge injection. The fluoropolymer material can be further modified by covalently bonding chemical groups or activator molecules to the fluoropolymer. The implant can then be surgically implanted into a patient.

Figure 2:
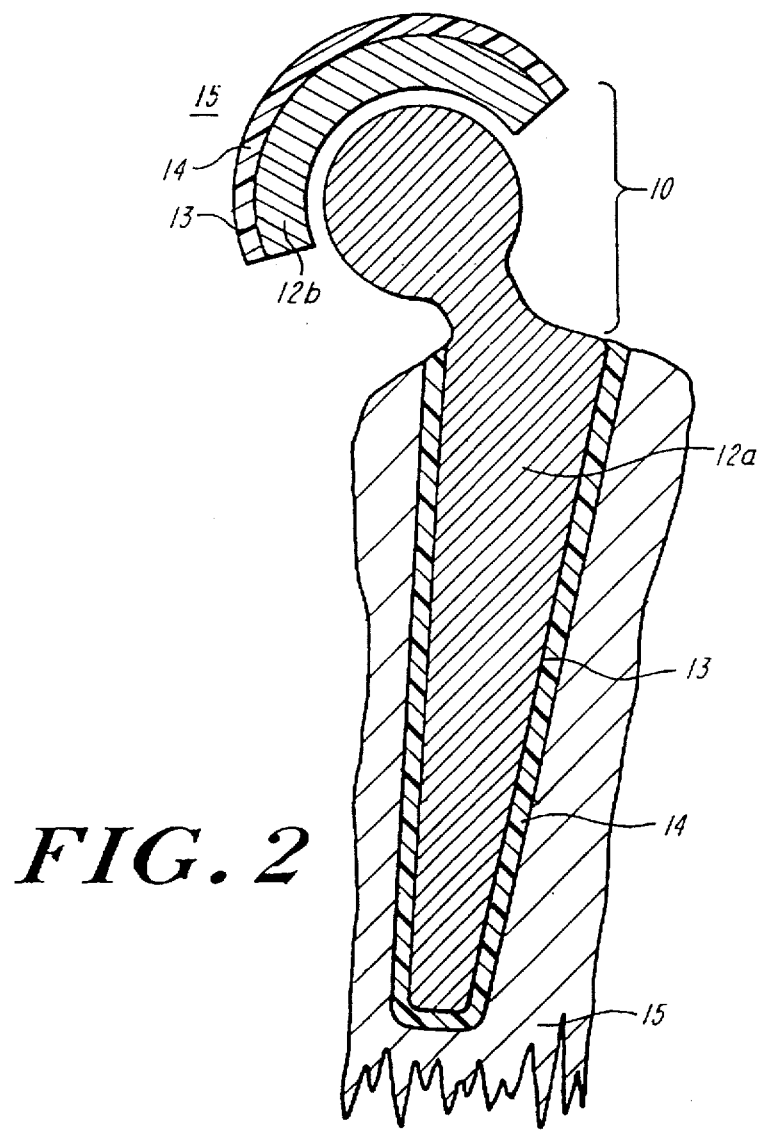
FIG. 2 is a cross-section of an orthopedic hip prosthesis implanted within a human femur and fabricated in accordance with the invention.

FIGS. 2–8 illustrate various embodiments of the present invention. FIG. 2 is a cross-section of an implantable hip prosthesis 10 implanted within a human femur 15. The prosthesis 10 comprises a femoral stem 12a and acetabular cup 12b each having tissue-contacting surfaces 13 coated with a fluoropolymer layer 14 which has been chemically modified to encourage growth and adherence of host tissue 15 to the implant. The surfices of the prosthetic implant which do not contact living tissue need not be coated with a fluoropolymer or, if coated, need not be electrically charged nor otherwise modified to enhance tissue ingrowth at those surfaces, since tissue ingrowth at such locations is not desirable.

Similar orthopedic implants for other joints, such as knee, shoulder, elbow and the like, can also be constructed in accordance with the invention.

Figure 3:
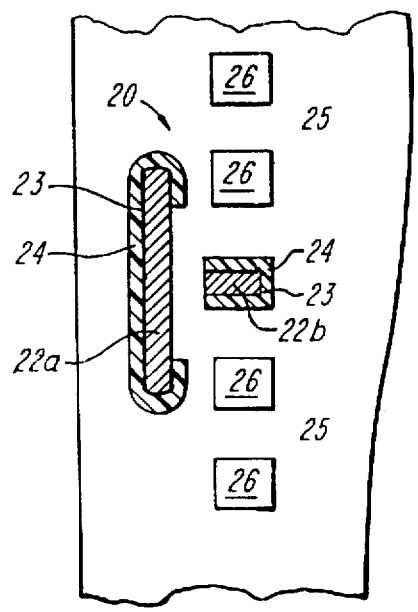
FIG. 3 is a cross-section of an orthopedic spinal fusion implant fabricated in accordance with the invention.

FIG. 3 is a cross-section of an orthopedic spinal fusion implant 20 having a rod element 22a and/or a plate element 22b with tissue-contacting surfaces 23 which have been coated with a layer of fluoropolymer material 24 which has been chemically modified according to the present invention to enhance growth of the adjacent spinal vertebrae 26 and surrounding tissue 25 into the implant.

Figure 4:
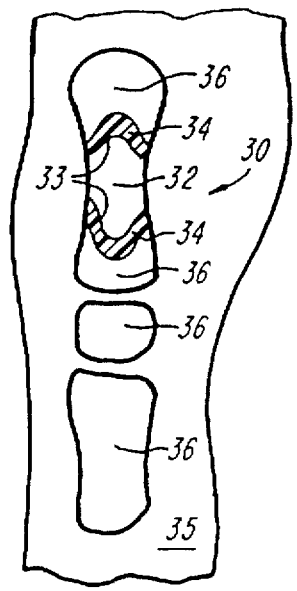
FIG. 4 is a cross-section of an orthopedic digit (finger or toe) prosthesis fabricated in accordance with the invention.

FIG. 4 is a cross-section of an orthopedic digit (finger or toe) implant 30 having a bone-replacement element 32 with tissue-contacting surfaces 33 which have been coated with a layer of fluoropolymer material 34 which has been chemically modified according to the present invention to enhance growth of the adjacent bones 36 and surrounding tissue 35 into the implant.

Figure 5:
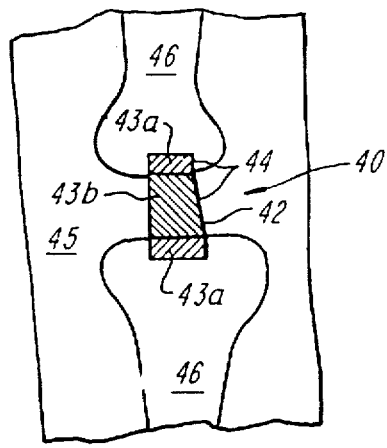
FIG. 5 is a cross-section of a tendon or ligament prosthesis implanted between bone surfaces and fabricated in accordance with the invention.

FIG. 5 is a cross-section of a tendon/ligament prosthetic implant 40 having an artificial ligament material 42 with tissue-contacting surfaces 43a and 43b which have been coated with a layer of fluoropolymer material 44 which has been chemically modified according to the present invention to enhance growth of the adjacent bones 46 and surrounding connective tissue 45 into the implant. Bony tissue-contacting surfaces 43a are preferably coated with negatively-charged fluoropolymer electret material, and soft tissue-contacting surface 43b is preferably coated with positively-charged fluoropolymer electret material, for optimum ingrowth of the respective tissues into the implant.

Figure 6:
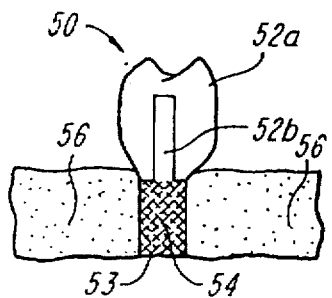
FIG. 6 is a cross-section of an orthopedic dental implant fabricated in accordance with the invention.

FIG. 6 is a cross-section of an orthopedic dental implant 50 having an artificial tooth 52a and post 52b with tissue-contacting surface 53 which has been coated with a layer of fluoropolymer material 54 which has been chemically modified according to the present invention to enhance growth of the adjacent bones 56 into the implant.

Figure 7:
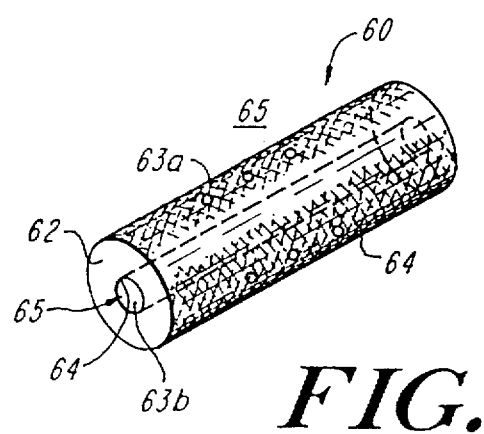
FIG. 7 is an elevational view of a vascular implant fabricated in accordance with the invention.

FIG. 7 illustrates a vascular implant 60 having an artificial membrane element 62 with tissue-contacting surface 63a and blood-contacting surface 63b which have been coated with a layer of fluoropolymer material 64 which has been chemically modified according to the present invention to enhance endothelialization of the adjacent blood and tissue 65 into the implant. It is important to note that either an entire vascular implant, or merely a blood-contacting portion thereof, can be constructed of a fluoropolymer electret material which can be electrically charged and chemically modified according to the present invention to enhance tissue ingrowth into all or only a portion of the implant, from the luminal (blood-contacting) side and/or the tissue-contacting side, as required. Both free-standing vascular grafts and vascular stents (structures placed within a patient's blood vessels to prevent luminal closure and thereby maintain blood flow therethrough), can be constructed in this manner. Because blood is a type of living tissue for which both its compatibility with a vascular implant and its tissue ingrowth capabilities are critical to patient therapy, it is a tissue for which the biocompatible implants described in this invention are especially appropriate.

Figure 8:
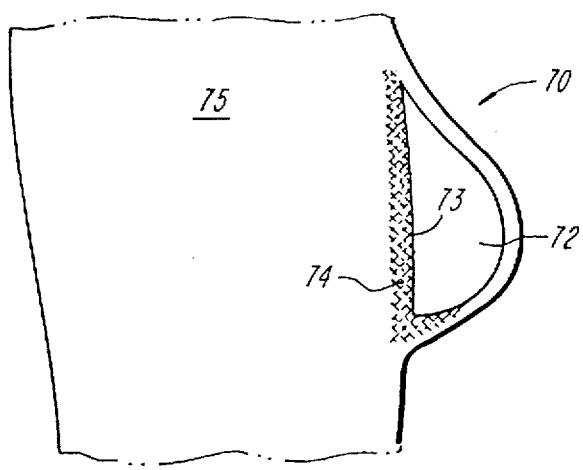
FIG. 8 is a cross-section of a soft tissue implant, such as a breast implant, fabricated in accordance with the invention.

FIG. 8 is a cross-section of a soft tissue implant 70, such as a breast implant. The implant 70 has a flexible reconstruction element 72 with tissue-contacting surface 73 which has been coated with a layer of fluoropolymer material 74 which has been chemically modified according to the present invention to enhance endothelialization and growth of adjacent tissue 75 into the implant.

It is important to note that the biocompatible implants of the present invention can be constructed entirely of an electrically-charged and chemically modified fluoropolymer material, or they can be constructed of various interior structural components, which can not be tissue-contacting, and other exterior surface components which can be tissue-contacting and which comprise an electrically-charged and chemically modified fluoropolymer material as described herein.

The invention will next be described in connection with the following non-limiting examples.

EXAMPLE I

Morphological Comparison of Osteoblasts Cultured on Negatively-Charged, Positively-Charged, and Electrically Neutral Flourinated Ethylenepropylene Copolymer (FEP) Electret Material Fluoropolymer discs, 30 mm in diameter, were lathe cut from 25 µm thick FEP sheets (DuPont Teflon® FEP Type 200A; Wilmington, Del.). All discs were washed in 2% Alconox detergent solution, rinsed copiously with distilled water and air-dried. Surface contaminants were removed ultrasonically in hexane and absolute methanol for one minute each.

FEP discs were subjected to a corona charge injection procedure to fabricate an electret. Mounted FEP discs were placed on a grounded aluminum block 4 cm below a single needle-point brass electrode connected to a low current, high voltage DC reversible polarity power supply (Bertan Associates model 205A-50R, Syosset, N.Y.). A copper mesh assembly connected to a low voltage DC reversible polarity power supply (Bertan Associates model 205B-03R, Syosset, N.Y.) was centered below the needle electrode, 2.5 cm above the FEP. The upper electrode was biased at 12 kV against the grounded FEP substrate and the copper mesh was biased to +1000 V. The FEP discs were exposed to this corona field for 20 minutes. The charged FEP discs were cleaned and sterilized by baking in a dry, 56° C. oven for 12 hours.

Human osteoblasts cultured on negatively-charged FEP showed a highly flattened morphology, and interdigitating groups of cells were observed. This morphology is associated with normal osteoblast growth signifying that the cells can attach to and grow properly on the negatively-charged FEP. In contrast, osteoblasts cultured on positively-charged FFP assumed a "stand-off" appearance with numerous fillopodial extensions. Cells on electrically neutral FEP demonstrated neither a flattened appearance nor a "stand-off" appearance.

Electrically charged FEP substrates can also be fabricated with surface modifications to improve the level and duration of cell attachment. For example, hydroxyl (OH) groups can be covalently bonded to the surfaces of Teflon® fluoropolymer discs, prepared as described above, by a radiofrequency glow discharge (RFGD) plasma process using hydrogen gas and methanol vapor. Primary amine ($NH_2$) groups can be added by exposing the RFGD-treated materials to a silane coupling agent, aminopropyltriethoxysilane (APTES). APTES can be reacted by immersing the OH-modified FEP discs in a solution containing 40 ml hexane and 2 ml APTES for about 2 seconds. Addition of APTES to the hexane is carried out below the hexane/air interface to minimize prepolymerization. Osteoblasts on APTES-modified electrically charged FEP remain adherent for at least one week in culture.

EXAMPLE II

Increased Osteoblast Attachment to Flouropolymer Electret Material Having OH, $NH_2$, and/or GRGDS Pentapeptide Surface Modifications Hydroxyl (OH) groups were covalently bonded to the surfaces of Teflon® fluoropolymer discs, prepared as in Example I, by a radiofrequency glow discharge (RFGD) plasma process using hydrogen gas and methanol vapor. Plasma modifications were performed for 2 minutes. Primary amine ($NH_2$) groups were added by exposing the RFGD-treated materials to a silane coupling agent, aminopropyltriethoxysilane (APTES). APTES was reacted by immersing the OH-modified FEP discs in a solution containing 40 ml hexane and 2 ml APTES for about 2 seconds. Addition of APTES to the hexane was carried out below the hexane/air interface to minimize prepolymerization.

The GRGDS pentapeptide was covalently coupled through the primary amine group of its N-terminal glycine spacer to surface OH groups after carbodiimide activation. Modifications were made to the entire surface or in discrete striped regions via the use of a metallic mask with twenty-five 300×1500 micrometer openings. Unmodified FEP controls and OH, $NH_2$ and GRGDS immobilized FEP discs were mounted in custom-made tissue culture dishes and sterilized prior to cell plating. Human osteoblasts isolated from resected trabecular bone were expanded for several weeks and maintained in 10% FCS/F 12 media (B. Aofmkolk, P. Hauschka, E. R. Schwartz, (1985) *Calcif Tissue Int.* 33:228). Cells were seeded onto experimental substrates at a density of 20,000/$cm^2$. Cell attachment and morphology were assessed using Hoffman modulation optics and scanning electron microscopy at various times after plating.

Osteoblasts cultured on unmodified FEP substrates showed early attachment but retained a rounded morphology. Cell adherence was not observed after 5–7 days in culture. Cells plated on OH-containing FEP substrates showed better attachment and flattening but most cells detached after 7–10 days in culture. In contrast, cells on $NH_2$-modified FEP substrates showed increased spreading and remained adherent for several weeks. On stripe-modified substrates, cells showed a highly preferential attachment to the OH and $NH_2$ stripes with occasional bridging between stripes. Cells on OH stripes detached after about one week while cells on $NH_2$ stripes remained adherent for significantly longer times.

Cells cultured on GRGDS peptide-grafted substrates displayed the greatest degree of flattening and showed good long-term attachment. These cells extended numerous cell processes and were predominantly arranged in organized sheets.

The surface chemistry of the FEP substrate strongly influenced the attachment and morphologic properties of cultured human osteoblasts. As expected, unmodified, hydrophobic FEP supported minimal cell attachment and spreading. OH-containing surfaces supported early adherence but eventual cell detachment. Increased cell attachment and flattening was observed on $NH_2$- and GRGDS-containing surfaces.

EXAMPLE III

Increased Osteoblast Function and Attachment to Fluoropolymers Having GRGDS Pentapeptide Surface Modifications FEP discs (30 mm diameter) were ultrasonically cleaned in hexane, methanol and distilled water. Surface OH groups were added via an RFGD flow-through process using hydrogen gas and methanol vapor. An $NH_2$-containing group was covalently linked to surface OH groups by reacting with aminopropyl triethoxysilane groups by reacting with aminopropyl triethoxysilane (APTES), via immersion in a 5% APTES solution in hexane. The GRGDS pentapeptide was covalently coupled through the primary amine group of its single carbodiimide activation. A second molecule with a single amino acid substitution, GRGES, was used as a control. The carboxy-terminus of the peptides was amidated in order to prevent non-specific reactivity. Unmodified FEP controls and OH, $NH_2$ and peptide immobilized FEP discs were placed in standard 12-well tissue culture dishes. Empty polystyrene wells served as additional controls.

Rat osteoblasts were isolated from the calvaria of 7 day neonatal CD1 rats using sequential collagenase/trypsin digestions. Osteoblasts were expanded in 10% FCS/F12 media and used after the first passage. Cells were seeded onto experimental substrates at a density of 20,000 cells/$cm^2$. Cell attachment and morphology were assessed using Hoffman modulation optics and scanning electron microscopy at various times after plating. Osteoblast proliferation was assessed using $^3$H-thymidine incorporation. Osteocalcin (a bone-specific protein located in the extracellular matrix) media levels were assessed using a commercially available radioimmunoassay. Total DNA was analyzed and used to normalize total cell number in all experiments.

Osteoblasts cultured on unmodified FEP showed early attachment but retained a rounded morphology. Cell adherence was not observed after 5–7 days in culture. Osteoblasts plated on OH containing FEP showed better attachment and flattening but most cells detached after 7–10 days in culture. In contrast, cells on $NH_2$ modified FEP showed increased spreading and remained adherent for several weeks. Cells cultured on GRGDS and GRGES peptide grafted substrates displayed the greatest degree of flattening and showed good long-term attachment. Cells extended numerous cell processes and were predominantly arranged in organized sheets. Osteoblasts on either peptide sequence were morphologically indistinguishable and were very similar in appearance to cells on polystyrene. Attachment levels on both RGD peptides were significantly greater than on OH substrates. Levels of cell proliferation were similar for both peptide sequences and polystyrene. FEP-OH showed significantly lower proliferation levels. The level of osteocalcin synthesis was significantly greater on GRGDS surfaces than all others including GRGES and polystyrene.

The surface chemistry of the FEP substrate strongly influenced the attachment and morphologic properties of cultured rat osteoblasts. Unmodified and OH-modified FEP supported minimal cell attachment and spreading. Increased cell attachment and flattening was observed on GRGDS- and GRGES-containing surfaces. Most significantly, these studies demonstrate that rat osteoblasts cultured on GRGDS substrates synthesize significantly higher levels of osteocalcin. This observation suggests that RGD-integrin binding allows the manipulation of phenotypic responses beyond cell attachment.

EXAMPLE IV

Increased Endothielial Cell Attachment to Hyaluronan Ester Films Having GRGDS Pentapeptide Surface Modifications The rapid in vivo degradation of hyaluronan (HA), an ubiquitous component of the mammalian extracellular matrix, has limited its use for medical device applications. A novel class of HA biopolymers termed HYAFF has been generated through benzyl or ethyl esterification of the carboxylic group on the glucoronic acid residue. Esterification results in much diminished rates of degradation in vivo. In an attempt to develop biodegradable scaffolds for tissue regeneration, woven HYAFF tubes have been produced as possible small diameter arterial grafts. Endothelialization of vascular grafts can play an important role in the reduction of thrombosis and in the control of neointimal thickening and anastomic hyperplasia (Koo, E. W. Y. and Gottlieb, A.I. (1991) *Lab. Invest.* 64:743; Williams, S. K. (1991) *Lab. Invest.* 64:721). The use of covalently linked adhesion peptides can increase the extent and rate of cell attachment. In the present study, surfaces of HA benzyl ester films (HYAFF 11, Fidia Advances Biopolymers) have been modified, by chemically coupling a peptide, GRGDS, containing RGD, the integrin recognition site of the fibronectin cell binding domain (Pierschbacher, M. D. and Ruoslahti, E. (1984) *Nature* 309:30–33.

Circular films of HYAFF 11 (21 mm diameter, 25–30 microns thick) were activated for 48 hours at room temperature with 1,1-carbonyldiimidazole (CDI; 40 mg/ml), and N-hydroxysulfosuccinimide, (1 mg/ml), in acetone. After rinsing with phosphate-buffered saline (PBS), the films were incubated with the GRGDS peptide, 0.2 mg/ml, in MES buffer, 0.1M, pH 1.5, or in MES buffer only for 48 hours at room temperature. All films were quenched with 1M glycine for at least hours before multiple washings with PBS. Selected films from various stages of the coupling protocol were examine using scanning electron microscopy (SEM). For in vitro attachment studies, films were placed on the bottom of 12-well plates and held in place with silicone rubber O-rings. The attachment and morphology of human umbilical vein endothelial cells (HUVEC) was investigated in serum-free and complete medium culture conditions. A low seeding density (5000 cells/$cm^2$) was chosen in order to minimize cell-cell order to minimize cell-cell interactions, thus allowing a more stringent evaluation of cell-substrate interactions. Cells were seeded on GRGDS-coupled films, CD1-activated films, and on standard tissue culture polystyrene (PS) wells. After 6, 24, 48 and 72 hours, the number of attached cells was counted using Hoffman modulation optics (200 ×). The total number of cells in ten fields chosen randomly in a prescribed 10×10 mm square field were counted. All groups were planted in triplicate in serum-containing and serum-free media.

CD 1/acetone modification resulted in minimal gross changes to the HYAFF film. SEM of virgin HYAFF films revealed a smooth texture with occasional striations probably resulting from initial film extrusion. CD1 modified films also showed smooth surfaces, although occasional minor pitting was observed.

As expected, minimal cell attachment was observed in serum-free conditions. No difference in cell attachment was observed, however, between GRGDS-coupled and control films. The degree of attachment was comparable to that on polystyrene wells. Adherent cells consistently displayed a round morphology and the number of attached cells decreased progressively during the course of the incubation.

Compared to serum-free conditions, all films showed an enhanced cell adhesion activity, except at 6 hours. Most cells showed a spread morphology, with numerous processes extending from the cell body. The extent of spreading was generally similar on GRGDS and control HYAFF films and both were comparable to the extent of spreading seen on polystyrene. Cell attachment levels were generally greater on GRGDS/HYAFF than on control HYAFF. In all cases, cell attachment levels were greater on polystyrene, especially at 72 hours.

Cell attachment studies suggest that RGD-modified HYAFF is capable of improved cell adhesion, although even CD1-activated controls showed better adhesion than unmodified HYAFF. The enhanced adhesion on polystyrene suggests that attachment is primarily dependent on absorbed serum proteins. In summary, HYAFF substrates represent a novel, biodegradable substrate for tissue engineering approaches.

EXAMPLE V

Increased Endothelial Cell Attachment to Modified Polyurethane Polydimethylsiloxane Having Fibronectin RGDS and REDV and Vitronectin RGDV Peptide Surface Modifications To improve the patency of small diameter vascular grafts, surfaces of such grafts fabricated with polyurethane polydimethylsiloxane (PU-PS) copolymer (Cardiothane) by the spray, phase inversion technique known to those of ordinary skill in the art were activated with radio frequency glow discharge (RFGD). Oligopeptides were then grafted to the surface of such grafts to promote endothelial cell attachment. Microporous vascular grafts (1.5 mm ID) and membrane sheets were fabricated with PU-PS by the spray, phase inversion technique. The PU-PS copolymer was modified by treatment with RFGD alone, absorption of oligopeptides without RFGD, or RFGD followed by covalent coupling of oligopeptides. The oligopeptides were from the cell recognition domains of fibronectin (RGDS, REDV) and vitronectin RGDV. Fibronectin and vitronectin were absorbed to PU-PS as positive controls. Human umbilical vein (HUVEC) and saphenous vein (HSEC) cells were seeded at $10^7$ cells/cm$^2$ and cell attachment assessed for up to 8 days in culture.

Endothelial attachment to grafts having an RFGD surface modification alone improved over endothelial attachment to unmodified grafts. The improved endothelial attachment to these grafts was maintained for up to 8 days. Adsorbed oligopeptides without RFGD showed increased initial attachment of cells over untreated PU-PS but with detachment of most cells at 8 days. RFGD treatment with covalently bonded oligopeptides showed an increased level of cell attachment of HUVEC and HSEC cells where compared to RFGD alone.

EXAMPLE VI

Increased Osteoblast Attachment to Fluoropolymers Having RGDX Surface Modifications Fluoropolymer (FEP) surfaces were partially hydroxylated via a flow-through radio frequency glow discharge process using hydrogen gas and methanol vapor (Vargo, T. G. et al. (1992) *Langmuir* 8:130–134. Valentini, R. F. et al. (1993) *J. Biomat. Sci.*, Polymer Ed. 5:13–36). Functionalizing the polymer surface with hydroxyl (OH) or amine (NH$_2$) groups leads to the formation of reactive surface groups that can serve as link points to couple peptide sequences to the substrate. Immobilization can be achieved by covalent coupling between OH and NH$_2$ groups on the fluoropolymer surface to NH$_2$ or sulthydryl (SH) groups on the peptide using various heterobifunctional crosslinkers. For example, one reaction utilizes 1.1' carbonyldiimidazole (CDI) to link fluoropolymer OH groups to the NH$_2$ terminus of RGDX peptides resulting in FEP-RGDX.

Peptides, such as peptides from the attachment-promoting peptide family RGDX (Arg-Gly-Asp-X) from the fibronectin/vitronectin/osteopontin family, or other small peptides (e.g. YIGSR Tyr-Iso-Gly-Ser-Arg) from the ECM glycoprotein, laminin, and large proteins (e.g., PDGF, TGI-β, BMP2-7, etc.) can also be linked by first reacting the polymer covalently with a silane coupling agent (APTES) that contains a primary NH$_2$. This reactive NH$_2$ can be coupled to SH groups located on cysteine (C) amino acid residues located on the N-terminus of the peptide (CRGDX) using succinimidyl 4-(N-maleimidomethyl) cyclohexane 1-carboxylate (SMCC) resulting in FEP-CRGDX. Conversely, an SH-containing silane coupling agent can be used to form a SH-NH$_2$-peptide link using SMCC. Peptides can also be custom-synthesized to contain spacer molecules which serve to tether the peptide from the surface. For example, glycine (G) has served as the spacer group in GRGDX, GGGGRGDX, and CGGGGRGDX molecules.

Fluted FEP rods (1.8 mm wide, 5 mm long) were implanted bilaterally into the distal medial femoral condyles of adult rats. FEP rods modified to include surface peptide sequences (e.g. RGDS, RGDT, RGDV, YIGSR) were tested. Unmodified FEP rods served as controls. Bone ingrowth was evaluated at 6, 12, and 36 days post-implantation using quantitative histomorphometry and fluorochrome labeling.

Preliminary data with osteoblasts indicated a significant enhancement of attachment with surface-grafted RGDX molecules. Studies were then performed to determine if these observations also held true in vivo. Bone/material interactions can be evaluated in vivo using sites with large amounts of trabecular/cancellous bone. The distal rat femur provides a well-studied site for bone material interactions and offers a sufficient bony area to implant small specimens. Adult (350–400 g) Sprague-Dawley rats were anesthetized with Nembutal (55 mg/kg IP). Using sterile technique, a standard lateral approach was used to expose the distal medial femoral condyle, with preservation of the periosteum. Care was taken not to violate the joint. One 1.8 mm wide hole, extending through the medial cortex into cancellous bone (roughly 5–6 mm) was created with the use of a hand-held 1.8 mm cutting trocar and saline irrigation. Drilling is avoided to prevent thermal necrosis. A fluted FEP rod of matching dimensions (1.8 mm diameter, 5 mm long) was press-fit into place. A similar procedure was performed on the contralateral side. The fascia and skin were closed in standard fashion using 5–0 vicryl bioresorbable sutures. Animals were housed in large, plastic cages and received food and water ad libitum.

Animals received bilateral implants for time periods of 6, 12, and 36 days. At the end of each of these time periods, the animals were sacrificed using carbon dioxide asphyxiation.

Upon explantation, samples were fixed in 4% formaldehyde and embedded in methacrylate resin for light microscopy. Serial 8–10 μm thick cross sections from each implant were mounted on glass slides. Alternate cross-sections were stained with Hematoxylin & Eosin stain, Masson's Trichrome, and vonKossa/Safranin-O to evaluate bone and fibrous tissue ingrowth. Histomorphometric analysis was performed using an image analysis system coupled to a video camera and Zeiss IM-35 inverted microscope using NIH Image Analysis software (NIH System 1.5b). (N.B. the fluted FEP has a scalloped perimeter with 6 convex and 6 concave sites. The maximal diameter across convex flutes is 18 mm and the diameter across concave sites is 14 mm. Since the drill hole is 18 mm round, there is space for tissue ingrowth at the 6 concave regions). The percentage of the length of the outer surface of the fluted rod in contact with new bone and the percentage of the available open area invaded by bone was quantified. All data was analyzed using the SAS statistical package (SAS Institute, Cary N.C.) on an IBM PC. A one- and two-way analysis of variance (independent variables, time and surface composition) was performed. Post hoc multiple comparison tests were used to compare the various implants within each time period.

All animals survived the procedure and no adverse reactions were noted. At all time points, retrieval of FEP specimens revealed good skin and bone healing. Several implants were well positioned and located in trabecular bone which contains significant marrow and stromal tissue while others were located adjacent to cortex or the growth plate. Only specimens adjacent to trabecular bone were assessed for bone formation. In some samples, the cutting process used to section the specimen resulted in loss of the actual implant although the implant outline and cellular margins remained.

No fibrotic or inflammatory response was noted for either plain FliP or RGD-FEP rods. At 6 days, most implants were surrounded by cells and extracellular matrix substance which had invaded the formerly empty spaces between the flutes.

In control FEP at 6 days, there was a relatively dense, vascularized tissue ingrowth consisting of putative fibroblasts surrounded by extracellular matrix. Cells at the implant interface were flattened and separated from the implant by a cell acellular membrane.

Trichrome staining revealed a faint blue pattern, suggesting the presence of low levels of collagen. Occasional sites with vonKossa stain in extracellular sites were observed. Very few cells were observed directly adhering to the FEP surface (1 site in 2 specimens).

RGD-FEP rods showed a generally similar appearance with qualitatively higher cell densities and collagen-positive staining. The membrane between the implant and host tissue was cellular and occasional islands of calcified tissue were noted. Several islands of noncalcified cartilage tissue were noted as well. Several specimens (4 out of 6) showed small clusters of cells adhering to one or more sites on the FEP-RGD rod.

As with the results at 6 days, at 12 days no fibrotic or inflammatory response was noted for either plain FEP or RGD-FEP rods. All implants were surrounded by cells and extracellular matrix substance which had invaded the concave spaces between the flutes.

In control FEP at 12 days, there was a relatively dense, vascularized tissue ingrowth consisting of fibroblasts and extracellular matrix. Cell density in some implants was greater than seen at 6 days. Cells at the implant interface were flattened and separated from the implant by a clear acellular membrane. Occasional islands of new bone (as assessed by structure and positive vonKossa stain) and cartilage were observed in most specimens. A few cells were observed directly adhering to the FEP surface at 1 site in 1 specimen.

RGD-FEP rods showed a generally similar appearance with qualitatively higher cell densities and collagen-positive staining. Several specimens (3 out of 6) showed new bone formation in multiple sites surrounding the entire specimen and all specimens showed some new bone formation that was not observed in control rods. Several islands of noncalcified cartilage tissue were noted in 2 out of the 6 specimens.

Most specimens (FEP control and FEP-RGD) showed extensive tissue ingrowth and new vascularization at 6 and 12 days. Most new tissue was not cartilaginous or bony in nature. In general, RGD-containing implants showed a denser tissue response than controls. In addition, at 12 days, several FEP-RGD implants contained bony islands surrounding the implant. These results suggest that RGD molecules grafted to the surface of implanted biomaterials generate a denser tissue response and promote the induction of bone-like tissue.

At present, 36 day specimens have been implanted but have not been evaluated histologically.

The invention can be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

I claim:

1. A biocompatible orthopedic or dental implant comprising a prosthesis having at least one tissue-contacting surface of a negatively charged polymeric electret material, said negatively charged polymeric electret material characterized by a bulk monopolar charge which produces an external electrostatic field, such that bone cell ingrowth and adherence to the prosthesis is promoted.

2. A biocompatible implant as in claim 1 wherein the negatively charged polymeric electret material comprises a fluoropolymer.

3. A biocompatible implant as in claim 2 wherein the fluoropolymer comprises fluorinated ethylenepropylene copolymer or polytetrafluoroethylene.

4. A biocompatible implant as in claim 1 wherein the negatively charged polymeric electret material comprises a dense polymeric coating.

5. A biocompatible implant as in claim 1 wherein the negatively charged polymeric electret material comprises a porous polymeric coating.

6. A biocompatible implant as in claim 1 wherein the implant further comprises a core structural portion and a negatively charged coating.

7. A biocompatible implant as in claim 6 wherein the core structural portion is selected from the group consisting of a polymer, a metal, a ceramic, and a silicon substrate.

8. A biocompatible implant as in claim 1 wherein the implant is constructed entirely of a negatively charged material.

9. A biocompatible implant as in claim 1 wherein a chemical group is covalently attached to a surface of the negatively charged polymeric electret material.

10. A biocompatible implant as in claim 9 wherein the chemical group is selected from the group consisting of an amine group, a hydroxyl group, a carboxyl group, and a sulfhydryl group.

11. A biocompatible implant as in claim 9 wherein an activator molecule is covalently attached to the chemical group.

12. A biocompatible implant of claim 11 wherein the activator molecule is selected from the group consisting of a cell attachment factor, a growth factor, a bone morphogenetic factor, an adhesion molecule, and an antibody.

13. A biocompatible implant as in claim 11 wherein the activator molecule comprises a biologically active peptide.

14. A biocompatible implant as in claim 13 wherein the biologically active peptide is derived from a protein with an integrin recognition site.

15. A biocompatible implant as in claim 13 wherein the biologically active peptide is derived from an extracellular matrix protein.

16. A biocompatible implant as in claim 15 wherein the extracellular matrix protein comprises fibronectin, vitronectin, or osteopontin.

17. A biocompatible implant as in claim 16 wherein the biologically active peptide comprises the amino acid sequence arginine-glycine-aspartic acid or glycine-arginine-glycine-aspartic acid-serine.

18. A biocompatible implant as in claim 15 wherein the extracellular matrix protein comprises laminin.

19. A biocompatible implant as in claim 18, wherein the biologically active peptide comprises the amino acid sequence tyrosine-isoleucine-glycine-serine-arginine.

* * * * *

UNITED STATES PATENT AND TRADEMARK OFFICE
CERTIFICATE OF CORRECTION

PATENT NO. : 5,759,205
DATED : June 2, 1998
INVENTOR(S) : Valentini

It is certified that error appears in the above-identified patent and that said Letters Patent is hereby corrected as shown below:

At column 2, line 6, delete: "...discloses In anchorage..." and insert: " ...discloses an anchorage...";

At column 2, line 15-16, delete "...disciose the..." and insert: "...disclose the...";

At column 2, line 20, delete: "...and carbcxylic acid..." and insert: "...and carobxylic acid...";

At column 5, line 3, delete: "...possess a. high..." and insert: "...possess a high...";

At column 8, line 12, delete: "The surfices of..." and insert: "The surfaces of...";

At column 9, line 28, delete: "...non-lirniting examples." and insert: "...non-limiting examples.";

At column 9, line 61-62, delete: "...-charged FFP assumed..." and insert "...-charged FEP assumed...";

UNITED STATES PATENT AND TRADEMARK OFFICE
CERTIFICATE OF CORRECTION

PATENT NO. :
DATED      :    5,759,205
INVENTOR(S) :   June 2, 1998
                Valentini It is certified that error appears in the above-identified patent and that said Letters Patent is hereby corrected as shown below:

At column 14, line 18-19, delete: "...TGI-$\beta$, ..." and insert: "...TGF-$\beta$, ...";

At column 15, line 34, delete: "...plain FliP or..." and insert: "...plain FEP or ...";

At column 16, line 37, delete: "...polymeric clectret material, ..." and insert: "...polymeric electret material, ...".

Signed and Sealed this

Sixth Day of April, 1999

Attest:

Attesting Officer

Q. TODD DICKINSON

Acting Commissioner of Patents and Trademarks